United States Patent [19]

Brody et al.

[11] Patent Number: 4,597,030
[45] Date of Patent: Jun. 24, 1986

[54] SURGICAL ILLUMINATOR

[75] Inventors: Garry S. Brody, Los Angeles; Alexander S. Borsanyi, Newport Beach, both of Calif.

[73] Assignee: American Hospital Supply Corporation, Evanston, Ill.

[21] Appl. No.: 697,216

[22] Filed: Jan. 31, 1985

[51] Int. Cl.[4] .............................. F21V 8/00
[52] U.S. Cl. ....................... 362/32; 128/20; 128/23; 350/96.26; 362/804
[58] Field of Search ........... 362/32, 119, 804; 128/6, 11, 13, 16, 18, 20, 23; 350/96.22–96.27

[56] References Cited

U.S. PATENT DOCUMENTS

| 3,043,910 | 7/1962 | Hicks, Jr. .................... 350/96.27 X |
| 3,357,423 | 12/1967 | Winchester et al. ................. 128/23 |
| 3,590,232 | 6/1971 | Sadowski . |
| 3,592,199 | 7/1971 | Ostensen . |
| 3,614,414 | 10/1971 | Gores . |
| 3,614,415 | 10/1971 | Edelman . |
| 3,634,938 | 1/1972 | Hutchinson . |
| 3,718,814 | 2/1973 | Van Slyke . |
| 3,794,091 | 2/1974 | Ersek et al. . |
| 3,800,135 | 3/1974 | Ramsey . |
| 4,086,919 | 5/1978 | Bullard .................... 128/6 |
| 4,337,763 | 7/1982 | Petrassevich . |

OTHER PUBLICATIONS

American V. Mueller, pp. 257, 258, 325, 784, 826, 827, 1096.

Primary Examiner—Tony M. Argenbright
Attorney, Agent, or Firm—Gordon L. Peterson

[57] ABSTRACT

A surgical illuminator comprising a plurality of elongated, flexible, optical fibers having proximal and distal end portions and a strip of tape for retaining at least the distal end portions of the optical fibers in a ribbon-like pattern. A connector is coupled to the proximal end portions of the optical fibers, and the connector is adapted to optically couple the optical fibers to a light source. The tape has adhesive on both of its faces so that the tape can also be adhered to a surgical instrument to provide illumination from the light source.

22 Claims, 8 Drawing Figures

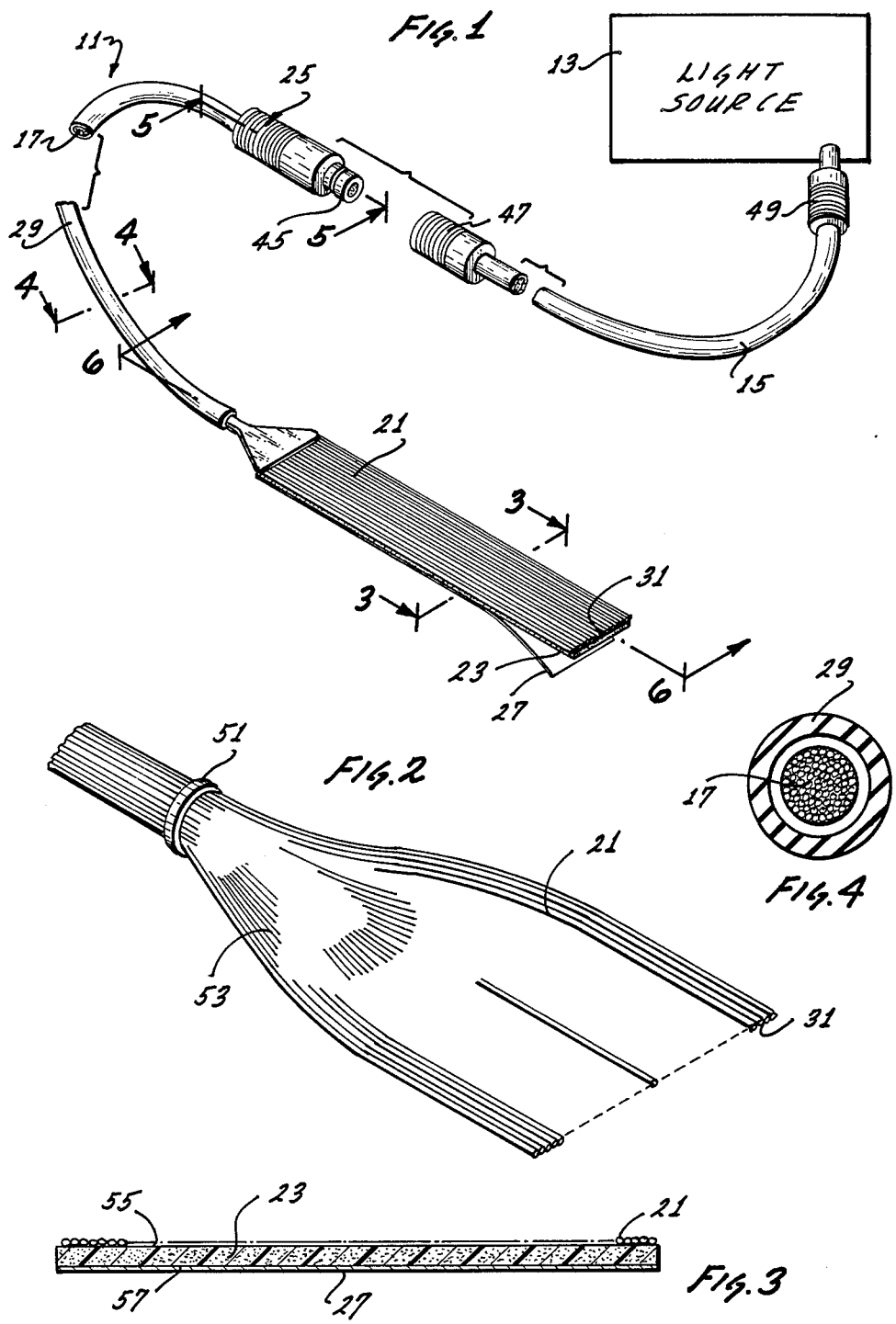

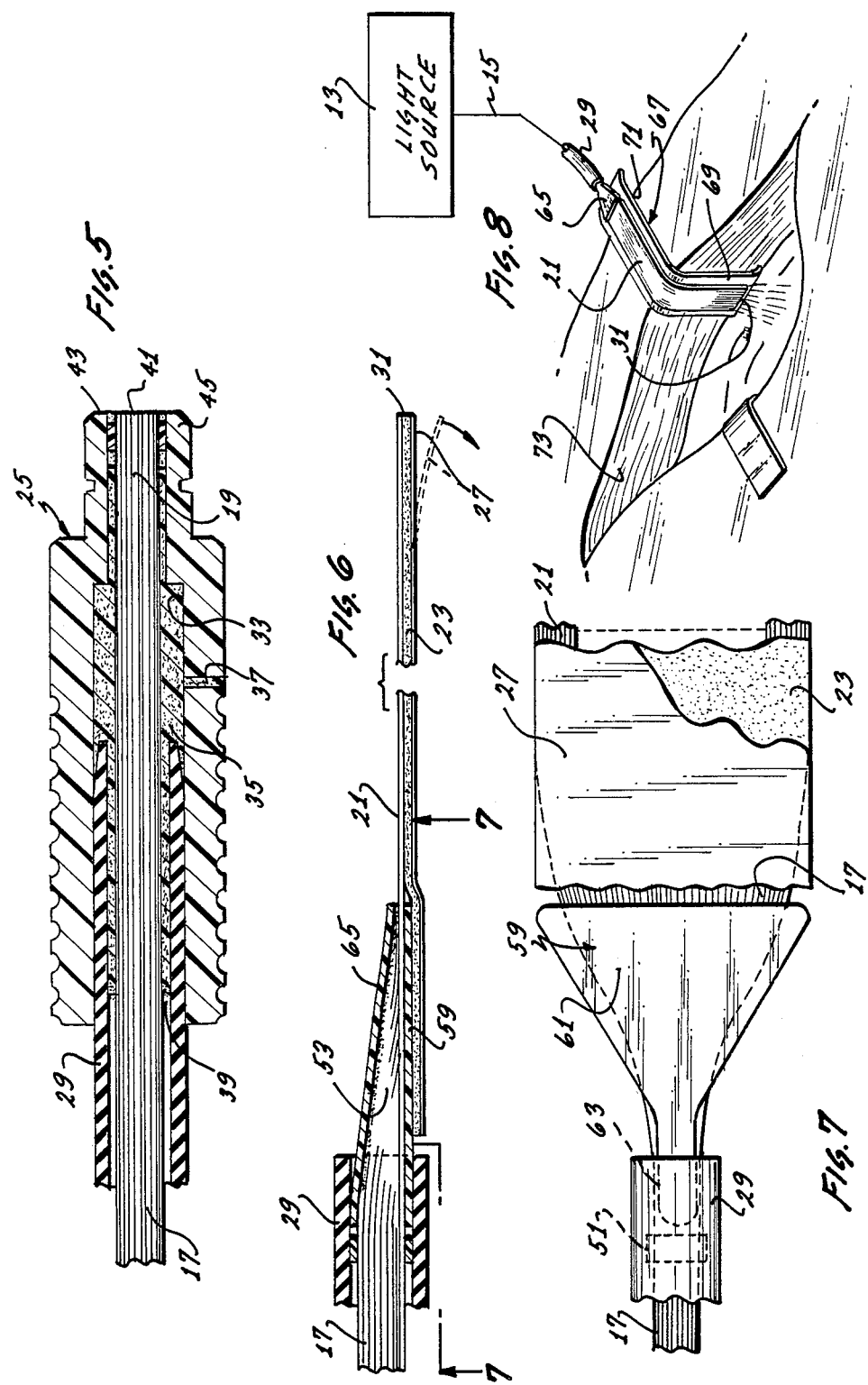

SURGICAL ILLUMINATOR

BACKGROUND OF THE INVENTION

In surgery, it is essential that the region in and around the incision be brightly illuminated. Conventional lighting includes the usual lighting fixtures within the operating room and a lamp on the surgeon's headgear.

It is also known to provide a fiberoptic illuminator which is attachable to a certain specific instrument. For example, it is known to provide an illuminator of this type for a dental handpiece as shown in Hutchinson U.S. Pat. No. 3,634,938, Gores U.S. Pat. No. 3,614,414 and Sadowski U.S. Pat. No. 3,590,232. It is also known to attach an illuminator, including a power pack, to a surgical retractor as shown in Ostensen U.S. Pat. No. 3,592,199.

One problem common to all of these illuminators is that each of them is adapted for attachment to only one particular instrument, such as a dental handpiece, or to a particular surgical retractor. Accordingly, if it were desired to provide an illuminator for several different instruments in the operating room, it would be necessary to have a different illuminator for each different surgical instrument.

The prior art illuminators are subject to various other disadvantages. For example, some require that relatively heavy or bulky components of the illuminator be mounted on the surgical instrument. Other prior art illuminators have one or more components that tend to obstruct the line of sight of the user.

SUMMARY OF THE INVENTION

This invention provides a surgical illuminator which generally overcomes the disadvantages noted above. The surgical illuminator of this invention can be quickly and easily affixed to surgical instruments of many different sizes and configurations. When so affixed, the illuminator is capable of providing a substantial quantity of light without obstructing the surgeon's line of sight. There are no large or bulky components of the illuminator which impede the manual retention or manipulation of the surgical instrument, and the light source is remotely located. Although the illuminator of this invention is particularly adapted for use as a surgical illuminator, it can be used with various other members to provide illumination.

The surgical illuminator of this invention preferably includes a plurality of elongated optical fibers having proximal and distal end portions and means for retaining at least the distal end portions of the optical fibers in a ribbon-like pattern. A connector is coupled to the proximal end portions of the optical fibers, and the connector is adapted to optically couple the optical fibers to a light source. The retaining means has an exterior face with pressure-sensitive adhesive thereon, and a release sheet is adhered to the exterior face by the adhesive. The release sheet is separable from the exterior face to expose the adhesive so that the distal end portions of the optical fibers can be adhered to a surgical instrument to provide illumination from the light source. To adapt the illuminator for use in surgery, at least the portion of the illuminator which is attached to the surgical instrument, and preferably the entire illuminator is sterilized.

The optical fibers and the retaining means are preferably flexible so that they can readily conform to the surgical instrument to which they are attached. This flexibility, combined with the pressure-sensitive adhesive on the exterior face of the retaining means, enables the surgical illuminator to be attached to surgical instruments of various different sizes and configurations. Although the illuminator can be attached to many different surgical instruments, it is particularly adapted for attachment to any of a variety of hand-held surgical instruments, including dental handpieces.

The retention of at least the distal end portions of the optical fibers in a ribbon-like pattern, although not essential, has several advantages. For example, ribbon has a minimal height dimension which is essentially incapable of obstructing the surgeon's line of sight or of obstructing the surgeon's manual manipulation of a hand-held surgical instrument. A ribbon pattern enables a relatively large number of fibers to be used to thereby provide bright illumination.

The retaining means preferably includes a strip of tape having a first face with a pressure-sensitive adhesive on such face. The distal end portions of the optical fibers are adhered to the first face and retained in the ribbon-like pattern by the pressure-sensitive adhesive. Preferably, the distal end portions of the optical fibers are retained on the retaining means in a single row. The tape is preferred because it forms an inexpensive base or substrate for the optic fibers and because the optical fibers can be quickly and easily mounted or retained on the tape by simply placing the fibers against the tape. In this regard, the ribbon-like pattern is particularly desirable because it is the pattern which can be most easily made when using the tape as the retaining means.

In a preferred construction, the tape has opposite faces, and both of the faces are coated with a pressure-sensitive adhesive. This provides an inexpensive way of mounting the optical fibers on the tape and of mounting the tape on the surgical instrument.

Another advantage of the invention is that the illuminator can be sized in the operating room, if desired. For example, the tape can be slit longitudinally to provide bifurcated light paths. Alternatively or in addition thereto, the width of the distal end portion of the illuminator can be reduced by slitting the tape and cutting off the unwanted optical fibers.

The surgical illuminator of this invention is of inexpensive construction, and it is disposable. This eliminates the need for sterilizing of the illuminator after each usage. In this regard, repeated sterilization may damage the light fibers, and this potential source of damage to the illuminator is eliminated by making the illuminator disposable.

The proximal ends of the optical fibers are coupled to the light source by a connector, and the region of the fibers between the ribbon-like pattern and the connector are preferably retained in a bundle which has greater thickness and less width than the ribbon-like pattern. The retention of this region of the optical fibers in a bundle can be by a plurality of bands and/or an elongated tube. The tube encases the optical fibers and protects them.

The optical fibers between the bundle and the ribbon-like pattern are arranged in a transition pattern which joins the bundle to the ribbon-like pattern. At least some of the optical fibers at the transition pattern are adhered to the tape.

The invention, together with additional features and advantages thereof, may best be understood by reference to the following description taken in connection with the accompanying illustrative drawing.

BRIEF DESCRIPTION OF THE DRAWINGS

FIG. 1 is a partially schematic, isometric view of a surgical illuminator constructed in accordance with the teachings of this invention and a light source.

FIG. 2 is a fragmentary, isometric view of the distal end portions of the optical fibers and adjacent regions of the optical fibers.

FIGS. 3 and 4 are enlarged sectional views taken generally along lines 3—3 and 4—4, respectively, of FIG. 1.

FIGS. 5 and 6 are enlarged fragmentary sectional views taken generally along lines 5—5 and 6—6, respectively, of FIG. 1.

FIG. 7 is a fragmentary sectional view taken generally along line 7—7 of FIG. 6.

FIG. 8 is a partially schematic isometric view illustrating one manner in which the surgical illuminator can be used.

DESCRIPTION OF THE PREFERRED EMBODIMENT

FIG. 1 shows a sterile surgical illuminator 11 coupled to a light source 13 via a fiberoptic cable 15. The light source 13 and cable 15 are not sterile. Generally, the illuminator 11 includes a plurality of elongated, flexible optical fibers 17 having proximal end portions 19 (FIG. 5) and distal end portions 21 (FIGS. 1 and 2), flexible means in the form of an elongated, flexible strip of tape 23, a connector 25 and a release sheet 27.

The optical fibers 17 extend continuously from the connector 25 through a flexible tube 29 and terminate in distal ends 31. More specifically, the proximal end portions 19 of the optical fibers 17 and the proximal end of the tube 29 are bonded within an axial passage 33 (FIG. 5) of the connector 25 by a suitable adhesive 35. The adhesive 35, which may be injected through a radial injection port 37 in the connector 25, surrounds portions of the optical fibers 17 and the tube 29 and flows into a radial clearance space 39 between the tube 29 and the optical fibers 17 to strongly bond the connector 25, the optical fibers 17 and the tube 29 together. The optical fibers 17 terminate proximally in proximal ends 41 which are flush with a proximal face 43 of the connector 25.

The connector 25 has a projection 45 which is adapted to be received and releasably retained within a distal connector 47 of the cable 15. The cable 15 has a proximal connector 49 which enables it to be optically coupled to the light source 13. In this manner, light can be provided from the light source 13 via the cable 15 to the proximal end portions 19 of the optical fibers 17.

The proximal end portions 19 are retained in a cylindrical configuration by the passage 33. A plurality of bands 51 (one being shown in FIG. 2) and the tube 29 retain the region of the optical fibers 17 within the tube 29 in a bundle which is essentially cylindrical.

The optical fibers 17 extend completely through the tube 29 in a cylindrical configuration, and upon emerging from the tube 29 form a generally fan-shaped transition portion or pattern 53 which joins the cylindrical configuration to the distal end portions 21. The distal end portions 21 are arranged in a ribbon-like pattern on the tape 23. The bundle within the tube has a greater thickness and a lesser width than the ribbon-like pattern. Although the ribbon-like pattern may include multiple rows of optical fibers or one or more bundles of optical fibers, in the embodiment illustrated, the distal end portions 21 are retained on the tape 23 in a single row so that each of the distal end portions 21 is in intimate contact with the tape 23, and the overall height of the tape-distal end portions 21 laminate is minimized. The ribbon-like pattern provides a relatively wide region of contact with the tape 23. Although the distal end portions 21 could be adhered to the tape 23 by encasing them to form one or more bundles and adhering the casing to the tape, in the illustrated embodiment, each of the optical fibers is adhered to the tape by direct contact with the tape.

The tape 23 is flexible and has opposite faces 55 and 57, with pressure-sensitive adhesive covering both of the faces. The release sheet 27 is adhered to the face 57 of the tape 23 by the adhesive on such face. The release sheet 27 is coated so that it can be easily peeled from the face 57.

The distal end portions 21 are adhered to the tape 23 by the adhesive on the face 55. As shown in FIGS. 6 and 7, the tape 23 underlies, and is substantially coextensive with, the distal end portions 21 and a substantial region of the transition portion 53. If desired, a short length of the optical fibers 17 adjacent the ends 31 may extend beyond the tape 23 to assure that the adhesive in the tape is fully covered and cannot pick up debris during manufacturing or thereafter.

The transition portion 53 is preferably supported by a relatively rigid tab or support member 59 of plastic or other suitable material. The tab 59 has a generally triangular or fan-shaped section 61 (FIG. 7) which is adhered to the face 55 of the tape 23 and a projection 63 received within, and if desired bonded within, the distal end portion 21 of the tube 29. An upper tab or support member 65 of substantially the same configuration as the tab 59 is bonded to the upper side of the transition portion 53 and is also bonded within the distal end portion of the tube 29. A major region of the tab 65 slopes toward the tab 59 as it extends distally of the tube 29 as shown in FIG. 6. The tabs 59 and 65 support the transition portion 53 and prevent the optical fibers 17 of the transition portion from snagging on objects with which it may come into contact. The tabs 59 and 65 are optional.

The illuminator 11 can be used with various different medical and industrial members. For example, the illuminator 11 may be used with a retractor 67 (FIG. 8). Although the retractor 67 could be of various different configurations, in the form shown in FIG. 7, it includes a first portion or leg 69 extending in a first direction and a second portion or leg 71 extending in a second direction. In the form shown in FIG. 8, the legs 69 and 71 intersect essentially at a right angle, and the leg 69 terminates at the distal end of the retractor 67.

By peeling the release sheet 27 from the face 57 of the tape 23, the tape 23 can be adhered to regions of both of the legs 69 and 71 by the adhesive on the face 57. In the embodiment shown, the distal ends 31 terminate proximally of the distal end of the retractor 67. Because the tape 23 and the optical fibers 17 are flexible, they can conform to the configuration of the retractor 67. Because the tape 23 and the ribbon-like pattern of the distal end portions 21 are thin and flat, the presence of these portions of the illuminator 11 on the retractor 67 is not likely to block the surgeon's line of sight nor to interfere with the surgeon's manual manipulation of the retractor 67.

In use, the retractor 67 can be used to pull apart an incision 73 during surgery. When so used, the distal ends 31 of the optical fibers 17 are within the incision. Light can be transmitted from the light source 13 via the cable 15 and the optical fibers 17 to the distal ends 31 to provide illumination within the incision 73. The surgical illuminator 11 can be discarded after use.

The tape 23 can be slit longitudinally to bifurcate the distal region of the surgical illuminator 11 or to reduce its width. This allows a single surgical illuminator to be adapted by the surgeon to provide illumination to two different areas or to accommodate various different surgical instrument widths.

Although an exemplary embodiment of the invention has been shown and described, many changes, modifications, and substitutions may be made by one having ordinary skill in the art without necessarily departing from the spirit and scope of this invention.

We claim:

1. An illuminator adapted to be coupled to a light source and to a member, said illuminator comprising:
   a plurality of elongated, flexible optical fibers having proximal and distal end portions;
   flexible means for retaining at least the distal end portions of the optical fibers in a ribbon-like pattern;
   a connector coupled to the proximal end portions of the optical fibers, said connector being adapted to optically couple the optical fibers to the light source;
   said retaining means having an exterior face with pressure-sensitive adhesive thereon; and
   a release sheet adhered to said exterior face of the retaining means by the adhesive and separable from the exterior face to expose the adhesive whereby the distal end portions of the optical fibers can be adhered to the member to provide illumination from the light source.

2. An illuminator as defined in claim 1 wherein at least said distal end portions of the optical fibers and said retaining means are sterile whereby the illuminator is a surgical illuminator.

3. An illuminator as defined in claim 1 wherein said distal end portions are retained on the retaining means in a single row.

4. An illuminator as defined in claim 1 wherein said retaining means adhesively retains at least the distal end portions of the optical fibers in said ribbon-like pattern.

5. An illuminator as defined in claim 1 wherein said retaining means includes a strip of tape having a first face with a pressure-sensitive adhesive on said first face, said distal end portions of the optical fibers being adhered to said first face and retained in said ribbon-like pattern by the pressure-sensitive adhesive on said first face.

6. An illuminator as defined in claim 5 wherein said exterior face is on said tape and is opposite the first face whereby said tape is double-sided adhesive tape.

7. An illuminator as defined in claim 5 wherein said distal end portions are retained on the first face of the tape in a single row.

8. An illuminator as defined in claim 5 wherein said tape is slitable longitudinally whereby the illuminator can be bifurcated.

9. An illuminator as defined in claim 5 wherein the illuminator is sterile.

10. An illuminator as defined in claim 1 including means for retaining the optical fibers in a bundle which has greater thickness and less width than the ribbon-like pattern, and wherein said optical fibers between the bundle and the ribbon-like pattern are arranged in a transition pattern which joins the bundle and the ribbon-like pattern.

11. An illuminator as defined in claim 10 including at least one support member extending along at least a portion of the transition pattern.

12. An illuminator as defined in claim 10 including first and second tabs on opposite sides of the transition pattern.

13. An illuminator as defined in claim 12 wherein said means for retaining the optical fibers in a bundle includes a flexible tube which terminates adjacent the transition pattern, at least one of said tabs having a portion within said tube, said retaining means for the distal end portions includes a strip of tape, said distal end portions of the optical fibers and said first tab are adhered to the tape.

14. An illuminator adapted to be coupled to a light source and to a member, said illuminator comprising:
    a plurality of elongated flexible optical fibers having proximal and distal end portions;
    a strip of tape having first and second faces with a pressure-sensitive adhesive on said first face, said distal end portions of the optical fibers being adhered to the first face and retained in a ribbon-like pattern by the pressure-sensitive adhesive on said first face;
    a connector coupled to the proximal end portions of the optical fibers, said connector being adapted to optically couple the optical fibers to the light source; and
    means for attaching the tape and the distal end portions of the optical fibers to the member to provide illumination from the light source to the member.

15. An illuminator as defined in claim 14 wherein said distal end portions of the optical fibers and the tape are sterile whereby the illuminator is a surgical illuminator.

16. An illuminator as defined in claim 14 wherein said attaching means includes an adhesive for adhering the second face of the tape to the member.

17. An illuminator as defined in claim 14 wherein said tape adhesively retains at least the distal end portions of the optical fibers in a single row on the tape.

18. An illuminator as defined in claim 14 wherein the strip of tape has a distal end and said distal end portions of the optical fibers extend beyond the distal end of the strip of tape.

19. A surgical apparatus adapted to be coupled to a light source, said apparatus comprising:
    a manually operable surgical instrument;
    a plurality of elongated, flexible optical fibers having proximal and distal end portions;
    flexible means for retaining at least the distal end portions of the optical fibers in a ribbon-like pattern;
    a connector coupled to the proximal end portions of the optical fibers, said connector being adapted to optically couple the optical fibers to the light source; and
    said retaining means having an exterior face with pressure-sensitive adhesive thereon adhering the retaining means and the distal end portions of the optical fibers to the surgical instrument whereby illumination is provided from the light source to the region of the surgical instrument.

20. An apparatus as defined in claim 19 wherein said surgical instrument has a first portion extending in a first direction and a second portion extending in a second direction, said first portion intersects said second portion and terminates at one end of the surgical instrument, said tape and said optical fibers are adhered to the surgical instrument along regions of both said first and second portions of said surgical instrument.

21. An illuminator adapted to be coupled to a light source and to a member, said illuminator comprising:
   a plurality of elongated flexible optical fibers having proximal and distal end portions;
   a strip of tape having first and second faces with a pressure-sensitive adhesive on both of said faces, said distal end portions of the optical fibers being adhered to the first face and retained thereon by the adhesive on said first face;
   a connector coupled to the proximal end portions of the optical fibers, said connector being adapted to optically couple the optical fibers to the light source; and
   a release sheet adhered to said second face of the tape by the adhesive on said second face and separable from the second face to expose the adhesive thereon whereby the distal end portions of the optical fibers can be adhered to the member to provide illumination from the light source.

22. An illuminator as defined in claim 21 wherein said distal end portions of the optical fibers and the tape are sterile whereby the illuminator is a surgical illuminator.

* * * * *